United States Patent
Farassat

(10) Patent No.: US 6,758,385 B2
(45) Date of Patent: Jul. 6, 2004

(54) APPARATUS FOR PERFORMING A PULL TEST

(75) Inventor: Farhad Farassat, Taufkirchen (DE)

(73) Assignee: F&K Delvotec Bontechnik GmbH, Ottobrunn (DE)

( * ) Notice: Subject to any disclaimer, the term of this patent is extended or adjusted under 35 U.S.C. 154(b) by 0 days.

(21) Appl. No.: 10/106,864

(22) Filed: Mar. 15, 2002

(65) Prior Publication Data

US 2003/0146263 A1 Aug. 7, 2003

(30) Foreign Application Priority Data

Feb. 1, 2002  (EP) ............................................. 02002465

(51) Int. Cl.$^7$ .......................... B23K 31/12; G01N 3/08
(52) U.S. Cl. ...................... 228/103; 228/102; 228/104; 228/4.5; 228/180.5; 73/827; 73/828
(58) Field of Search ..................... 228/4.5, 8, 102–104, 228/1.1, 180.5; 73/827, 828; 219/56.1, 56.21, 56.22

(56) References Cited

U.S. PATENT DOCUMENTS

| | | | | |
|---|---|---|---|---|
| 3,572,108 A | * | 3/1971 | McShane et al. | 73/827 |
| 4,453,414 A | * | 6/1984 | Ronemus et al. | 73/827 |
| 4,895,028 A | * | 1/1990 | Mayer | 73/827 |
| 4,907,458 A | * | 3/1990 | Biggs et al. | 73/827 |
| 5,275,058 A | * | 1/1994 | Pham et al. | 73/827 |
| 5,591,920 A | * | 1/1997 | Price et al. | 73/828 |
| 5,894,981 A | * | 4/1999 | Kelly | 228/104 |
| 6,178,823 B1 | * | 1/2001 | Sykes | 73/827 |
| 6,564,115 B1 | * | 5/2003 | Kinnaird | 700/121 |

FOREIGN PATENT DOCUMENTS

| | | | |
|---|---|---|---|
| EP | 0263542 A1 | * | 8/1987 |
| EP | 0772036 A2 | * | 5/1997 |
| EP | 0 772 036 A2 | | 5/1997 |
| JP | 02-090038 A | * | 3/1990 |
| JP | 2001-11887 A | * | 4/2001 |

OTHER PUBLICATIONS

Walter, P., "Bond testing enters mainstream PCB assembly", Microelectronics Journal, Mackintosh Publications LTD. Luton, GB, Bd. 27, Nr. 1, (Feb. 1996).

Shankara Prasad, et al., "An Improved Wire Bond Pull Test", Solid State Technology, Cowan Publ. Corp., Washington, US, Bd. 34, Nr. 6, (Jun. 1991).

Perlberg, G. et al., "Wire Bond Pull Testing Understanding the Geometric Resolution of Forces", Advanced Packaging, IHS Publishing Group, US, Bd. 3, Nr. 1, (1994).

* cited by examiner

Primary Examiner—L. Edmondson
(74) Attorney, Agent, or Firm—Knobbe, Martens, Olson & Bear, LLP

(57) ABSTRACT

An apparatus for performing a pull test to determine the resistance of a bonded-wire loop extending between two bond contacts on a substrate to tensile force. The apparatus includes a traction hook controllably inserted under the bonded-wire loop, a drive device connected to the hook and generating a tensile force directed substantially perpendicular to the substrate surface, a force-measurement device associated with the hook to detect the tensile force at each moment, and a recording device connected to the force-measurement device in order to record a breaking force value for the bonded-wire connection. The force-measurement device is disposed substantially coaxially with the vector of the tensile force. The apparatus also includes a detector to detect the highest point of bonded-wire loop and a position controller for the automatic positioning of the traction hook and thus the tensile force vector origin substantially adjacent the highest point of the bonded-wire loop.

28 Claims, 3 Drawing Sheets

APPARATUS FOR PERFORMING A PULL TEST

RELATED APPLICATIONS

This application claims the benefit of the European Patent application 02 002 465.9 filed Feb. 1, 2002.

BACKGROUND OF THE INVENTION

1. Field of the Invention

The invention relates to an apparatus for performing a pull test, to determine tensile strength of a bonding wire connection tensile strength.

2. Description of the Related Art

The pull test has long been the most commonly used method of testing bonding wire connections. In this method a small tension hook is inserted under a loop of wire between two bonding contacts and is moved away with constant velocity in a direction perpendicular to the surface of the substrate (i.e., usually upwards) until the loop breaks or a predetermined force has been reached. The tensile force applied at each moment is determined with a force-measurement device, and the value of tensile force that is being applied when the wire loop breaks away is recorded as the pull-off strength, which provides information about the quality of the bonding connection.

With this procedure, for instance, weakening of the wire in the heel region can be very well detected, as can the quality of the welding. The results of the test are compared with the minimal tensile strength for bonding wire connections specified in the relevant quality publications (e.g., MIL-STD883 method 2011).

Known test apparatus for carrying out this procedure, in which the force measurement is customarily accomplished by detecting the deformation the tensile force produces in an extension arm to which the hook is attached, have proved to be disadvantageous in certain respects. The precision of the measurements seems on the whole to be in need of improvement, and problems have arisen regarding reproducibility under conditions of changing ambient temperature.

The object of the invention is thus to make available an improved test apparatus of this generic kind, which in particular is designed to provide more accurate and reproducible test results even if the ambient temperature is variable.

This object is achieved by a test apparatus including a drive rod with tension hook positioned at an end thereof that can be controllably inserted under the wire loop, a drive device that is connected to the tension hook and generates a tensile force alone a tensile force vector (F) directed substantially perpendicular to the substrate surface, a force-measurement device comprising at least one load cell disposed coaxially with the drive rod and associated with the tension hook to detect the tensile force at each moment, a recording device engaged with the force-measurement device in order to record a pull-strength value for the bonded-wire connection, wherein the force-measurement device is disposed substantially coaxial with the tensile force vector (F), a detector to detect the highest point of the bonding wire loop, and a position controller adapted for automatic positioning of the tension hook and hence the point of origin of the tensile force vector; below the highest point of the bonding wire loop.

The invention includes the idea of departing from the previously customary extension-arm principle and instead disposing the force-measurement device so that it is substantially coaxial with the tensile force vector generated by the drive unit. It further includes the idea of ensuring that the wire loop is reliably grasped at its highest point, so as to avoid errors in the measurement results introduced by force components deviating in direction from the perpendicular to the substrate surface. For this purpose, in accordance with the invention, detection means to detect the highest point in the bonding wire loop and position controllers for automatic positioning of the tension hook in such a way that the starting point of the tensil force vector is below the highest point of the wire loop are position are provided.

The force-measurement device preferably comprises at least one load cell so disposed as to be coaxial with a drive rod of the tension hook. In the interest of the extensive temperature compensation, the force-measurement device preferably comprises a combination (a pair) of load cells disposed one above the other.

In another preferred embodiment an air bearing of the drive rod of the hook is provided, so as for practical purposes to eliminate the frictional forces that are produced in conventional bearings and that reduce the accuracy of the measurements.

In still another advantageous development of the idea behind the invention, a motor-gearbox unit is provided to rotate the tension hook about an axis aligned with the direction of action of the drive device, i.e. to fix the hook at a predetermined angle with respect to the tensile force vector. This measure serves on one hand to facilitate manipulation of the test apparatus in the case of substrates with complex bonding geometry, and on the other hand contributes towards the above-mentioned goal of increasing measurement accuracy, because it makes it possible to avoid potentially error-introducing positions of the hook relative to the wire loop.

Achievement of both of the above-mentioned advantages is also assisted by the provision of an x-y table for the coordinate-controlled positioning of the substrate (and hence of the highest point of the loop that the hook is meant to engage) with reference to the hook.

This measure should be regarded as closely linked to the provision of a camera with a field of view directed towards the side of the wire loop, and an image evaluation device connected to the camera, with which to calculate the coordinates of the highest point in the wire loop in the camera image. Alternatively, it can also be combined with the provision of a movement or proximity sensor associated with the drive unit, in particular the drive rod of the tension hook, and of a control and evaluation unit associated therewith. The latter serves to detect the maximal value of a plurality of positions at which the hook can engage the bonding-wire loop, and to determine the x-y coordinates of the engagement position at which the height is maximal. It will be clearly evident that the result of the measurement of the position of the highest point in the wire loop can be taken as a starting point for a correspondingly calculated shifting of the position of the sample table.

In another advantageous embodiment of the invention, spring means are disposed in association with the hook and the drive unit, in order to prestress the hook into a specified initial position, and also to attenuate the engagement between hook and wire loop and/or to limit the amount of tensile force, in order to protect the force-measurement device. In particular, the spring means comprise at least one first spring with low spring constant, for prestressing into the initial position and attenuate the engagement, and a second spring with high spring constant to limit the tensile force, both springs preferably being disposed coaxially with the drive rod. This arrangement results in a construction that is simple to manufacture and to maintain, while leverage and moments of tilt that might introduce errors into the measurement results are fundamentally ruled out.

BRIEF DESCRIPTION OF THE DRAWINGS

Further features will be evident from the subordinate claims and the following description of an exemplary embodiment with reference to the figures, wherein

DETAILED DESCRIPTION OF THE PREFERRED EMBODIMENTS

Figure 1:
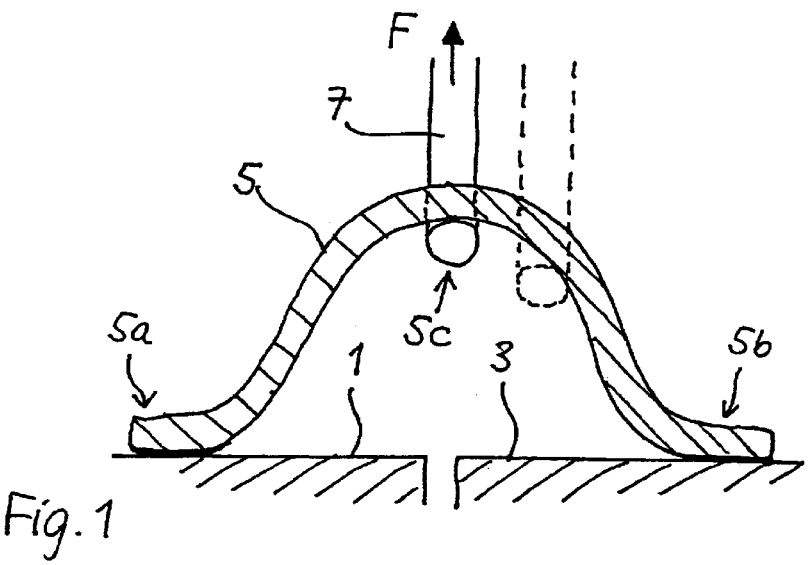
FIG. 1 is a schematic drawing of a wire loop to make clear the test principle.

FIG. 1 shows schematically a bonding wire 5 bent into a loop between two bonding surfaces 1, 3. A tension hook 7 has been positioned under the wire to carry out the so-called pull test. The bonded wire 5 is attached to the bonding surfaces 1, 3 at contact points (bonding contacts) 5a, 5b. The reference numeral 5c designates the highest point in the bonding wire loop. In the figure the hook 7 is in the optimal position for testing, namely under the highest point in the loop 5; for comparison, the dashed lines show a hook (not labelled with a number) that is displaced to the side and hence in a position unfavourable for testing.

Figure 2:
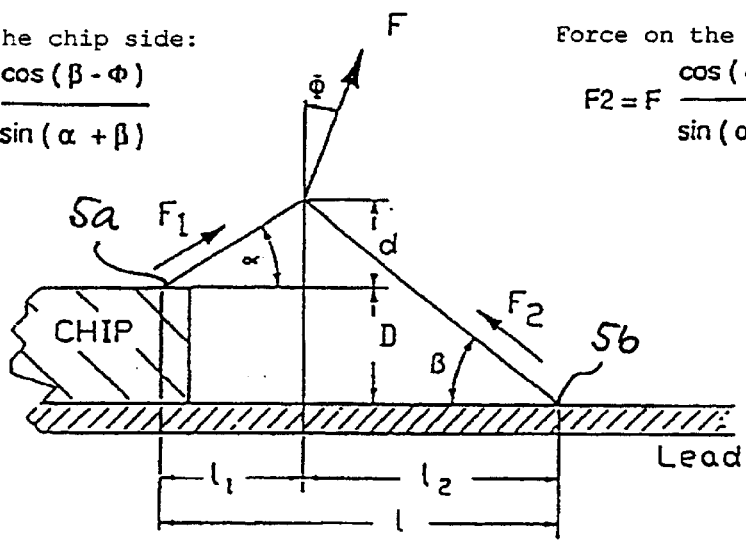
FIG. 2 is another schematic drawing to illustrate the forces acting during a pull test.

FIG. 2 is a diagram illustrating the general case, in which the bond contacts are at different levels. It shows the angles and force vectors relevant to performing and evaluating the pull test, and the labels make it essentially self-explanatory. To make clear the geometric relationships between FIG. 1 and FIG. 2, in FIG. 2 the bond contacts 5a, 5b are identified; the components connected by the bonding wire (not shown in FIG. 2) in this case are a semiconductor circuit chip and a lead.

Regarding FIG. 2, in other respects reference is made to the above general discussion of the pull test.

Figure 3:
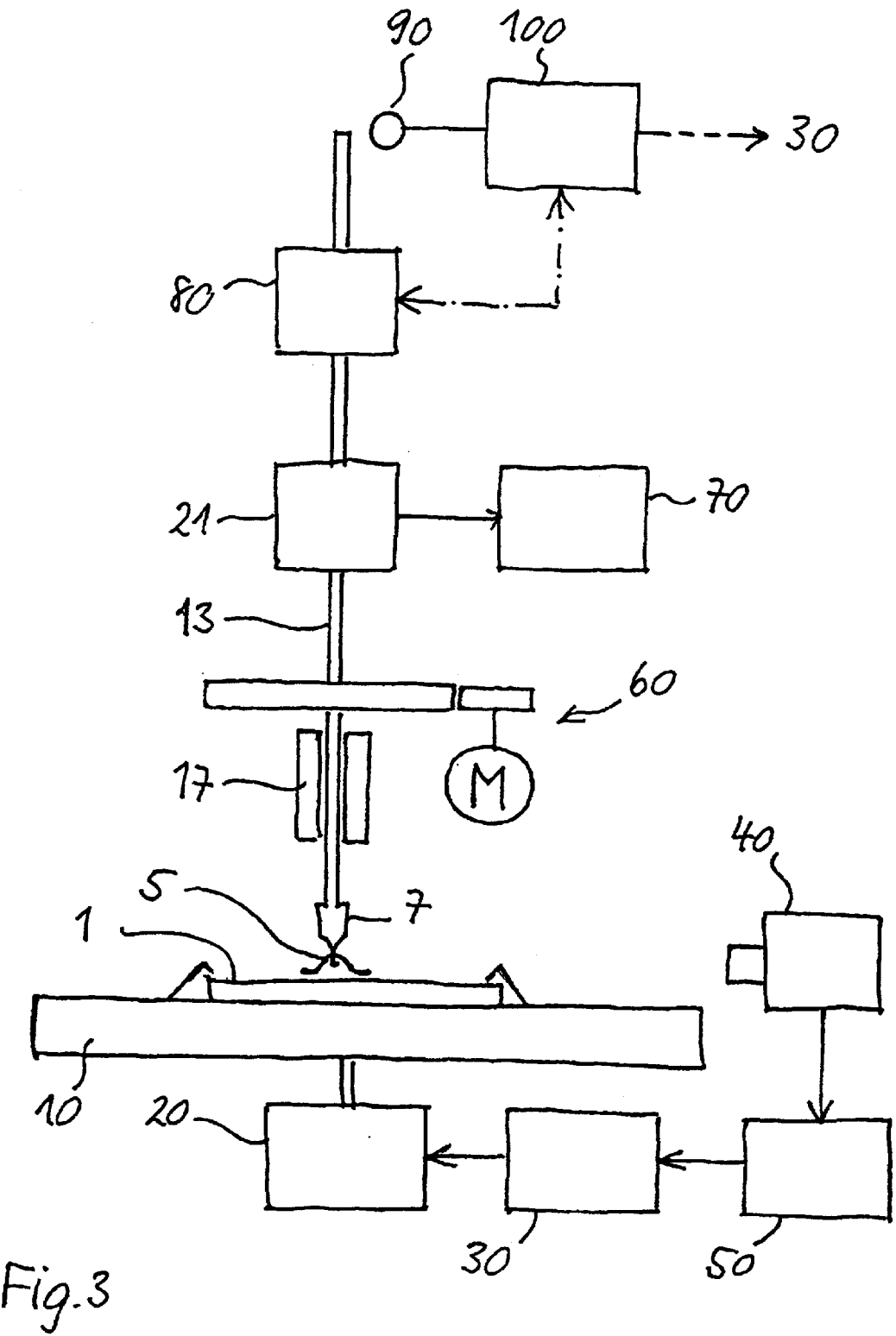
FIG. 3 is a schematic diagram of a test apparatus according to one embodiment of the invention.

FIG. 3 shows the basic construction of a test apparatus according to one embodiment of the invention in schematic diagram form; here it is being used to test the tensile strength of a wire loop 5 bonded to a substrate 1. The substrate 1 is fixed to an x-y table 10, movement of which is controlled by a table drive unit 20 controlled by coordinate control stage 30.

A charge coupled device (CCD) camera 40, the output of which goes to an image evaluation device 50, is disposed at the side of the substrate 1 and records an image of the loop 5. (To simplify the drawing, the actual camera position is not shown correctly in the figure.) The output of the image evaluation device 50 is connected to an input of the coordinate control state 30, so that it can signal to the latter the coordinates representing the position of the highest point in the loop 5, calculated on the basis of the camera image, and enable the x-y table 10 to be moved in accordance with the result of this evaluation.

The hook 7 is disposed at the lower end of a drive or measurement rod 13, which is supported in a practically frictionless manner in an air bearing 17(this, like the drive rod, will be described in greater detail below). A motor-gearbox unit 60 is provided to adjust the angular position of the hook. The drive or measurement rod 13 is attached to a force-measurement device 21 (which, likewise, is described in greater detail below with reference to FIG. 4), the output signal of which is sent a recording unit 70. The test apparatus as a whole is driven by a measurement drive unit 80.

To the upper end of the drive rod 13 is attached a movement or proximity sensor 90 which is connected to a control and evaluation unit 100; the latter is additionally connected so that control and measurement signals can be sent from it to the measurement drive unit 80 and to the coordinate control stage 30. The control and evaluation unit, in cooperation with the coordinate control stage (and the table drive unit 20) as well as the measurement drive unit 80, serves to determine the position of the highest point on the basis of the signals from the movement sensor 90, which detects movements of the drive rod (measurement rod) 13 that follow the engagement of the hook 7 with the loop 5. In addition, it serves to report the coordinates of the highest point to the coordinate control stage 30 of the x-y table 10, in order to bring about a movement of the substrate 1 and hence the loop 5 such as to achieve the optimal position for engagement with the hook 7.

Figure 4:
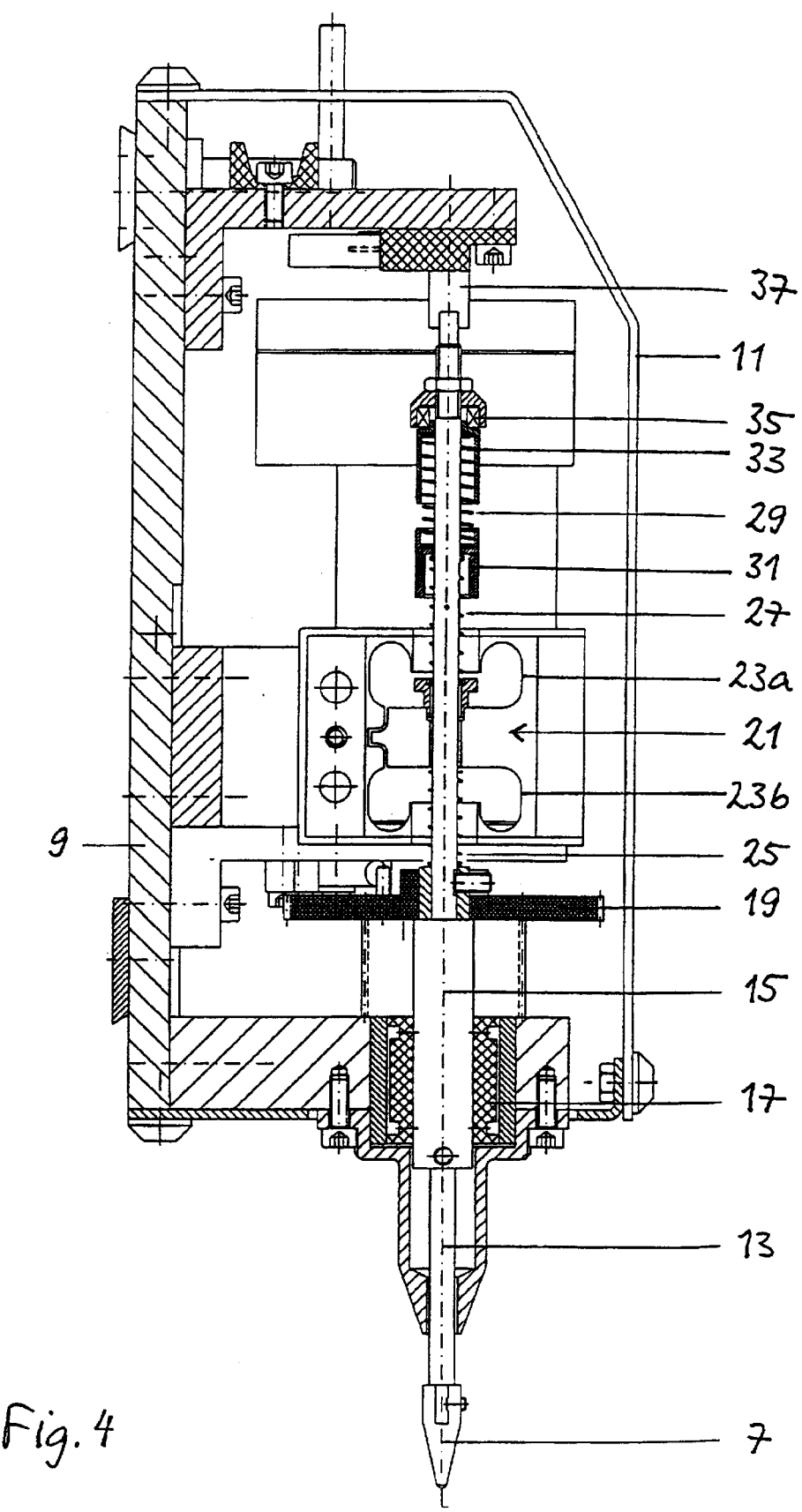
FIG. 4 shows a longitudinal section of the main part of an embodiment of the test apparatus in accordance with the invention.

FIG. 4 shows a longitudinal section to illustrate parts of an embodiment of the test apparatus in accordance with the invention that is at present preferred. This is assembled on a mechanically stable supporting structure 9 that comprises several parts, and is protected by a cover 11. Evaluation devices and drive or power-supply components situated outside this structure are not shown in the figure; however, reference is made to these in the following description.

The tension hook 7 is attached to a drive rod 13, which simultaneously serves as a "measurement rod" to transmit the measurement force and is guided in a frictionless manner through an air bearing 17 in an air-bearing shaft 15. This arrangement ensures an especially low-friction supporting and hence a highly accurate measurement of the pull-off strength.

At the upper end of the air-bearing shaft 15 there is nonrotatably fixed to the drive rod 13 a cylinder gear 19, which meshes with the output pinion of an electric motor (neither of which is shown) and by way of which the hook 7 can be caused to rotate about the long axis of the drive rod 13, so as to change the orientation of the hook. As a result, a fine adjustment of the position of the hook with respect to the bonding connections to be tested is possible, even with difficult geometric constellations. This, too, thus contributes towards achieving a high measurement accuracy and cleanly reproducible results of the evaluation, even with bonding connections of a variety of configurations.

The drive or measurement rod 13 is surrounded coaxially by a force measurement device 21, which comprises two oppositely oriented load cells 23a, 23b of the conventional construction. Associated with the lower load cell 23b is a so-called touchdown spring 25 for prestressing of the drive rod 13 and with it the tension hook 7, to fix the latter in the initial position. Associated with the upper load cell 23a is an exchangeable main measurement spring 27, the spring constant of which is chosen to be appropriate for the measurement range that applies in each case. To guide the main measurement spring 27 and simultaneously to make available a first support surface for a protective spring ("Softweg" spring) 29 on the drive rod, a first spring sleeve 31 is provided. The upper part of the protective spring 29 is guided within a second spring sleeve 33, which in turn is supported in a ball bearing 35 for torsional protection of the above-mentioned springs.

Above the upper end of the drive or measurement rod 13 is disposed a fork photoelectric barrier 37 as a safety shut-off device for the test apparatus (in cooperation with evaluation electronics that are not shown).

The test apparatus described above is completed by means (not shown) for detecting and evaluating the position of the highest point in the wire loop—such as a CCD camera with suitable resolution, connected to a device to evaluate its output—and an x-y table by means of which a substrate bearing the wire loop to be tested can be moved with respect to the tension hook 7 in such a way that the latter can be inserted under the highest point of the wire loop, thus allowing an optimal accuracy and reproducibility of the test result to be achieved (cf. FIG. 3).

The embodiment of the invention is not restricted to this example and the aspects emphasized above, but is also possible in a large number of modifications that are within the competence of a person skilled in the art.

What is claimed is:

1. An apparatus for performing a pull test in order to determine tensile strength of a bonding wire connection comprising a bonding wire loop between two bonding contacts on a substrate, the apparatus comprising:
   a drive rod with a tension hook positioned at an end thereof that can be controllably inserted under the wire loop;
   a drive device that is connected to the tension hook and generates a tensile force along a tensile force vector (F) directed substantially perpendicular to the substrate surface;
   a force-measurement device comprising at least one load cell disposed coaxially with the drive rod and associated with the tension hook, to detect the tensile force at each moment;
   a recording device engaged with the force-measurement device in order to record a pull-off strength value for the bonded-wire connection, wherein the force-measurement device is disposed substantially coaxially with the tensile force vector (F);
   a detector to detect the highest point of the bonding wire loop; and
   a position controller adapted for automatic positioning of the tension hook, and hence the point of origin of the tensile force vector, below the highest point of the bonding wire loop.

2. The apparatus of claim 1, wherein the force-measurement device comprises a pair of load cells disposed one above the other, coaxially with the drive rod of the tension hook.

3. The apparatus of claim 1, wherein the drive rod of the tension hook is supported in an air bearing.

4. The apparatus of claim 1, further comprising a measurement drive unit and a motor-gearbox unit arranged to rotate the tension hook about the direction of action of the measurement drive unit so as to fix the tension hook in a predetermined angular position with respect to the tensile force vector (F).

5. The apparatus of claim 1, wherein the position controller comprises an x-y table for coordinate-controlled movement of the substrate, and hence the highest point of the bonding wire loop, with respect to the tension hook.

6. The apparatus of claim 1, wherein the detector comprises a camera, the field of view of which is directed from the side onto the bonding wire loop, and an image-evaluation device connected to the camera in order to calculate the coordinates of the highest point of the bonding wire loop from the camera image.

7. The apparatus of claim 4, wherein the detector comprises a sensor adapted to sense at least one of movement and proximity associated with the measurement drive unit, and, connected therewith on the input side, a control and evaluation unit to detect the loop-height values of a plurality of engagement positions in which the tension hook engages the bonding wire loop and to determine the x-y coordinates of the engagement position with the maximal height value.

8. The apparatus of claim 4, further comprising a spring associated with the tension hook and the measurement drive unit so as to effect at least one of pre-tensioning the tension hook in a specified initial position as well as attenuating the engagement between tension hook and the bonding wire loop and limiting the tensile force in order to protect the force-measurement device.

9. The apparatus of claim 8, wherein the spring comprises a first spring with a low spring constant for pre-tensioning the tension hook into the specified initial position as well as for engagement attenuation, and a second spring with a high spring constant to limit the tensile force.

10. The apparatus of claim 9, wherein the first and second springs are disposed so as to be coaxial with the drive rod of the tension hook.

11. The apparatus of claim 7, wherein the sensor is associated with the drive rod of the tension hook.

12. A testing apparatus for performing a pull-test on a bonding wire loop, the apparatus comprising:
    a drive rod with a tension hook positioned at an end thereof that can be controllably inserted under the wire loop;
    a drive device that is connected to the tension hook and generates a tensile force along a tensile force vector (F) directed substantially perpendicular to the substrate surface;
    a force-measurement device associated with the tension hook, to detect the tensile force at each moment;
    a motor-gearbox unit arranged to rotate the tension hook to an angular position about the tensile force vector (F);
    a recording device engaged with the force-measurement device in order to record a pull-off strength value for the bonded-wire connection, wherein the force-measurement device is disposed substantially coaxially with the tensile force vector (F);
    a detector to detect the highest point of the bonding wire loop; and
    a position controller adapted for automatic positioning of the tension hook, and hence the point of origin of the tensile force vector, below the highest point of the bonding wire loop.

13. The apparatus of claim 12, wherein the force-measurement device comprises at least one load cell disposed coaxially with the drive rod of the tension hook.

14. The apparatus of claim 12, further comprising an air bearing supporting the drive rod.

15. The apparatus of claim 12, wherein the position controller comprises an x-y table for coordinate-controlled movement of the substrate, and hence the highest point of the bonding wire loop, with respect to the tension hook.

16. The apparatus of claim 12, wherein the detector comprises a camera, the field of view of which is directed from the side onto the bonding wire loop, and an image-evaluation device connected to the camera in order to calculate the coordinates of the highest point of the bonding wire loop from the camera image.

17. The apparatus of claim 12, further comprising a measurement drive unit and wherein the detector further comprises a sensor adapted to sense at least one of movement and proximity associated with the measurement drive unit and, connected therewith on the input side, a control and evaluation unit to detect the loop-height values of a plurality of engagement positions in which the tension hook engages the bonding wire loop and to determine the x-y coordinates of the engagement position with the maximal height value.

18. The apparatus of claim 17, further comprising a spring associated with the tension hook and the measurement drive unit so as to effect at least one of pre-tensioning the tension hook in a specified initial position as well as attenuating the engagement between tension hook and the bonding wire loop and limiting the tensile force in order to protect the force-measurement device.

19. The apparatus of claim 18, wherein the spring comprises a first spring with a low spring constant for pre-tensioning the tension hook into the specified initial position as well as for engagement attenuation, and a second spring with a high spring constant to limit the tensile force.

20. The apparatus of claim 12, wherein the motor-gearbox unit comprises a cylinder gear meshed with an output pinion of an electric motor.

21. A testing apparatus for performing a pull-test on a bonding wire loop, the apparatus comprising:
    a drive rod with a tension hook positioned at an end thereof that can be controllably inserted under the wire loop;
    a drive device that is connected to the tension hook and generates a tensile force along a tensile force vector (F) directed substantially perpendicular to the substrate surface;
    a force-measurement device associated with the tension hook, to detect the tensile force at each moment;
    a recording device engaged with the force-measurement device in order to record a pull-off strength value for the bonded-wire connection, wherein the force-measurement device is disposed substantially coaxially with the tensile force vector (F);
    a detector to detect the highest point of the bonding wire loop;
    a first spring with a low spring constant for pre-tensioning the tension hook into a specified initial position as well as for engagement attenuation;
    a second spring with a high spring constant to limit the tensile force; and
    a position controller adapted for automatic positioning of the tension hook, and hence the point of origin of the tensile force vector, below the highest point of the bonding wire loop.

22. The apparatus of claim 21, wherein the force-measurement device comprises at least one load cell disposed coaxially with a drive rod of the tension hook.

23. The apparatus of claim 21, further comprising an air bearing supporting the drive rod.

24. The apparatus of claim 21, wherein the position controller comprises an x-y table for coordinate-controlled movement of the substrate, and hence the highest point of the bonding wire loop, with respect to the tension hook.

25. The apparatus of claim 21, wherein the detector comprises a camera, the field of view of which is directed from the side onto the bonding wire loop, and an image-evaluation device connected to the camera in order to calculate the coordinates of the highest point of the bonding wire loop from the camera image.

26. The apparatus of claim 21, further comprising a measurement, drive unit and a motor-gearbox unit arranged to rotate the tension hook about the direction of action of the measurement drive unit so as to fix the tension hook in a predetermined angular position with respect to the tensile force vector (F).

27. The apparatus of claim 26, wherein the detector comprises a sensor adapted to sense at least one of movement and proximity associated with the measurement drive unit, and, connected therewith on the input side, a control and evaluation unit to detect the loop-height values of a plurality of engagement positions in which the tension hook engages the bonding wire loop and to determine the x-y coordinates of the engagement position with the maximal height value.

28. The apparatus of claim 27, wherein the motor-gearbox unit comprises a cylinder gear meshed with an output pinion of an electric motor.

* * * * *

UNITED STATES PATENT AND TRADEMARK OFFICE
CERTIFICATE OF CORRECTION

PATENT NO. : 6,758,385 B2
DATED : July 6, 2004
INVENTOR(S) : Farhad Farassat

It is certified that error appears in the above-identified patent and that said Letters Patent is hereby corrected as shown below:

Title page,
Item [73], Assignee, delete "Bontechnik" and insert -- Bondtechnik --.
Item [56], References Cited, FOREIGN PATENT DOCUMENTS,
delete "2001-11887 A" and insert -- 2001-118887 A --.

Signed and Sealed this

Fifteenth Day of November, 2005

JON W. DUDAS
*Director of the United States Patent and Trademark Office*